United States Patent [19]

Garcia et al.

[11] Patent Number: 5,399,587
[45] Date of Patent: Mar. 21, 1995

[54] BIOLOGICALLY ACTIVE COMPOUNDS

[75] Inventors: Maria L. Garcia, Edison; Robert A. Giacobbe, Lavellette; Otto D. Hensens, Red Bank; Gregory J. Kaczorowski, Edison; Seok H. Lee, Cranford; Owen B. McManus, North Plainfield; Deborah L. Zink, Manalapan, all of N.J.

[73] Assignee: Merck & Co., Inc., Rahway, N.J.

[21] Appl. No.: 166,499

[22] Filed: Dec. 13, 1993

[51] Int. Cl.$^6$ .............................. A01K 31/35
[52] U.S. Cl. ...................... 514/451; 514/468; 514/721; 514/763; 514/766; 549/356; 549/458; 554/229; 556/400; 568/2; 568/606; 568/612; 568/665; 568/816; 568/817; 568/819; 568/821
[58] Field of Search ............... 514/451, 468, 721, 763, 514/766; 549/356, 458; 854/229; 556/400; 568/2, 606, 612, 665, 810, 817, 819, 821

[56] References Cited

U.S. PATENT DOCUMENTS

| | | | |
|---|---|---|---|
| 4,831,033 | 5/1989 | Roberts | 514/255 |
| 4,929,718 | 5/1990 | Possani et al. | 530/326 |
| 5,006,512 | 4/1991 | Ohnishi | 514/21 |
| 5,006,523 | 4/1991 | Atwal | 514/227.5 |
| 5,055,475 | 10/1991 | Lubisch et al. | 514/326 |
| 5,112,824 | 5/1992 | Baldwin et al. | 514/253 |
| 5,158,969 | 10/1992 | Olesen et al. | 514/419 |

FOREIGN PATENT DOCUMENTS

| | | |
|---|---|---|
| 0310410 | 4/1989 | European Pat. Off. |
| 0467709 | 1/1992 | European Pat. Off. |
| 0467710 | 1/1992 | European Pat. Off. |
| 59-253826 | 6/1986 | Japan |
| WO89/09600 | 10/1989 | WIPO |
| WO91/13865 | 9/1991 | WIPO |
| WO92/05171 | 4/1992 | WIPO |

OTHER PUBLICATIONS

Robertson et al., "Potassium Channel Modulators: Scientific Applications and Therapeutic Promise", J. Med. Chem. vol. 33, 1990, pp. 1529–1541.

Wantanabe et al. "CAF-603: A New Antifungal Carotane Sesquiterpene, Isolation and Structure Elucidation", J. Natural Products, vol. 53, 1990, p. 1176–1181.

Quagliato et al., "the Synthesis and Structural Characterization of WAY-120,491, A Novel Potassium Channel Activator", Bioorganic & Medicinal Chemistry Letters, vol. 1, 1991, pp. 39–42.

McManus, O. B. et al. "An Activator of Calcium-Dependent Potassium Channels Isolated from a Medicinal Herb", Biochemistry, vol. 32, No. 24, pp. 6128–6133 (1993).

Watanbe et al., Journal of Natural Products, vol. 53, #5, pp. 1176–1181, 1990.

*Primary Examiner*—José G. Dees
*Assistant Examiner*—Deborah D. Carr
*Attorney, Agent, or Firm*—Francis P. Bigley; Mark R. Daniel; Joseph F. DiPrima

[57] ABSTRACT

The present invention relates to novel potassium channel agonists which are useful in activating the calcium activated Maxi-K potassium channel in mammalian neuronal and smooth muscle tissue. The claimed compounds are of the general formula:

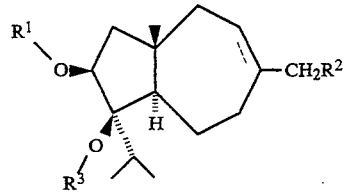

In addition, a novel microbiological process for producing the claimed compounds is described.

8 Claims, No Drawings

BIOLOGICALLY ACTIVE COMPOUNDS

BACKGROUND OF THE INVENTION

This invention relates to novel potassium channel agonists useful to treat diseases or disorders associated with potassium channels. The invention also relates to chemical intermediates useful in the synthesis of potassium channel agonists.

The art reveals that a compound of structural formula (I):

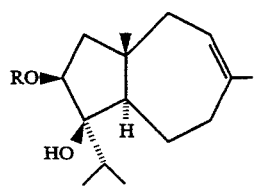

wherein R is hydrogen or an acyl group has been isolated from the fungal organism *Gliocladium virens* IFO9166. Watanabe et al. *Journal of Natural Products* 53, 5, 1176–1181 (1990), and was disclosed as useful as a possible antifungal or antimicrobial agent. The compound wherein R is hydrogen is known in the art as CAF-603 and is hereinafter referred to as Compound B, and was referred to by Wantanbe as CAF-603. The present invention, on the other hand, presents novel compounds useful as a potassium channel agonists.

Potassium channel agonists are useful for a number of physiological disorders in mammals, including humans. Ion channels, including potassium channels, are found in all mammalian cells and are involved in the modulation of various physiological processes and normal cellular ionic homeostasis. Potassium ions generally control the resting potential of cell membranes and the efflux of potassium ions causes repolarization of the plasma membrane after cell depolarization. Potassium channel agonists hyperpolarize the cell and diminish electrical excitability. There are a number of different potassium channel subtypes and one of the most important physiologically is the high conductance $Ca^{2+}$-activated $K^+$(Maxi-K) channel which is present in neuronal tissue and smooth muscle. Intracellular calcium concentration ($Ca^{2+}i$) and membrane potential gate these channels. For example, Maxi-K channels are opened by increases in intracellular calcium ion concentration or membrane depolarization. Elevation of intracellular calcium concentration is required for neurotransmitter release and for smooth muscle contraction. Therefore, modulation of Maxi-K channel activity affects transmitter release from the nerve terminal and the contractability of various smooth muscle tissues. The compounds of this invention are therefore useful in the treatment of neurological disorders in which hyperpolarization of neuronal cells elicits anticonvulsive and antiischemic effects. They are also useful to hyperpolarize and relax smooth muscles including, but not exclusively, those in the vasculature and airways to elicit antihypertensive and antiasthmatic actions, respectively. As smooth muscle relaxants, potassium channel agonists are useful in a variety of pathophysiological conditions that include: (1) relieving muscle cramps associated with dysmenorrhea; (2) treatment of urinary incontinence; (3) treatment of irritable bowel syndrome; and (4) treatment of angina.

A number of drugs in development function as potassium channel agonists. Examples of these include the structural classes represented by the cromakalim and pinacidil type potassium channel openers. These potassium channel agonists exert their effects primarily by opening ATP-dependent $K^+$ channels. They have demonstrated vasodilatory activity due to their activation of these channels in vascular smooth muscle cells. Furthermore, they also activate ATP-dependent $K^+$ channels in tracheal smooth muscle suggesting a possible utility as antiasthmatic drugs. These compounds have either weak effects or no effects on Maxi-K channels. The present invention represents the first sesquiterpene which is useful as a potassium channel agonist. The present invention relates to novel carotane sesquiterpenes which are useful as potassium channel agonists. Because these compounds target the Maxi-K channel, they have utility in suppressing neurotransmitter release, as well as in relaxing vascular and airways smooth muscle.

SUMMARY OF THE INVENTION

The present invention is directed to novel sesquiterpenes of structural formula (II), shown below.

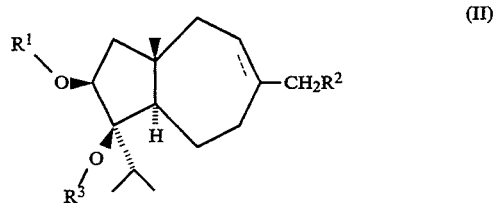

These compounds are useful as potassium channel agonists. More specifically, these compounds and pharmaceutically acceptable salts thereof are useful as Maxi-K potassium channel agonists and are thus useful in the treatment of neuronal disorders in which neurotransmitter release must be suppressed in order to elicit anticonvulsant and antiischemic activity. This compound and related compounds are also useful as smooth muscle relaxants for antiasthmatic, antihypertensive and antispasmodic applications. Furthermore, this compound is useful for other disorders sensitive to potassium channel activating activity. In addition, compounds disclosed and claimed in the instant disclosure are useful as synthetic intermediates in the synthesis and/or manipulation of the claimed potassium channel agonists. The present invention is also directed to pharmaceutical compositions containing the claimed potassium channel agonists as the active ingredient and to methods of treatment of human or mammalian diseases using the claimed compounds or pharmaceutical compositions.

DETAILED DESCRIPTION OF THE INVENTION

The present invention is directed to compounds of formula (II):

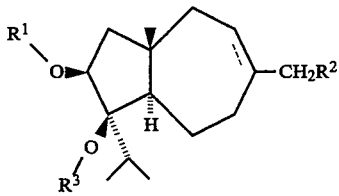

(II)

and pharmaceutically acceptable salts thereof, wherein:

$R^1$ is:
(a) H,
(b) $C_{1-5}$alkyl,
(c) $C_{2-5}$alkenyl
(d) $C_{1-30}$alkylcarbonyl,
(e) $C_{2-30}$alkenylcarbonyl,
(f) $R^4-O-R^4-$,
(e) substituted $R^4-O-R^4-$ wherein the substituent is phenyl or methoxy,
(f) tetrahydropyran, or
(g) $(R^4)_3$ Si—$R^4-$ wherein $R^4$ is independently $C_{1-5}$alkyl or $C_{2-5}$alkenyl at each occurrence, $R^3$ is:
(a) H,
(b) $C_{1-5}$alkyl,
(c) $C_{2-5}$ alkenyl
(d) $C_{1-30}$alkylcarbonyl,
(e) $C_{2-30}$alkenylcarbonyl,
(e) $R^4-O-R^4-$,
(f) substituted $R^4-O-R^4-$ wherein the substituent is phenyl or methoxy,
(g) tetrahydropyran, or
(h) $(R^4)_3$ SiR$^4$, or $R^1$ and $R^3$ together with the adjacent oxygen and ring carbon atoms, form a five-membered ring wherein $R^1$ and $R^3$ together are a single substituted or unsubstituted carbon or boron atom, wherein the carbon atom is substituted with two substituents independently selected from:
(a) H,
(b) $C_{1-4}$ alkyl,
(c) $C_{2-5}$ alkenyl,
(d) $C_{1-6}$ alkoxy,
(e) $C_{2-6}$ alkenyloxy, and
(f) phenyl, and wherein the boron atom is substituted with one substituent selected from:
(a) H,
(b) $C_{1-4}$ alkyl,
(c) $C_{2-5}$ alkenyl,
(d) $C_{1-6}$ alkoxy,
(e) $C_{2-6}$ alkenyloxy, and
(f) phenyl;

$R^2$ is:
(a) H,
(b) OH,
(c) $C_{1-5}$alkyloxy,
(d) $C_{2-5}$alkenyloxy,
(e) $C_{1-30}$alkylcarbonyloxy,
(f) $C_{2-30}$alkenylcarbonyloxy,
(g) $R^4-O-R^4-O-$,
(h) substituted $R^4-O-R^4-O-$ wherein the substituent is phenyl or methoxy,
(i) tetrahydropyran-oxy, or
(j) $(R^4)_3$ Si—$R^4-$, provided that when $R^2$ is H and $R^3$ is H, $R^1$ is not H or $CH_3CO$; $R^4$ is independently $C_{1-5}$alkyl or $C_{2-5}$ alkenyl at each occurrence, and the dashed line indicates the optional presence of a double bond.

Preferred are compounds wherein:

$R^1$ is:
(a) H,
(b) $CH_3$,
(c) $C_{1-30}$alkylcarbonyl,
(d) $C_{2-30}$alkenylcarbonyl
(e) $CH_3OCH_2$,
(f) $PhCH_2OCH_2$,
(g) $t-BuOCH_2$,
(h) $CH_3OCH_2CH_2OCH_2$,
(i) tetrahydropyran, or
(j) $Me_3SiCH_2CH_2$;

$R^2$ is:
(a) H,
(b) OH,
(c) methoxy,
(d) $C_{1-30}$alkylcarbonyloxy,
(e) $C_{2-30}$alkenylcarbonyloxy,
(f) $CH_3OCH_2O$,
(g) $PhCH_2OCH_2O$,
(h) $t-BuOCH_2O$,
(i) $CH_3OCH_2CH_2OCH_2O$,
(j) tetrahydropyranoxy, or
(k) $Me_3SiCH_2CH_2O$, provided that when $R^2$ is H and $R^3$ is H, $R^1$ is not H or $CH_3CO$; and $R^3$ is:
(a) H,
(b) $C_{1-5}$alkyl,
(c) $C_{2-5}$ alkenyl
(d) $C_{1-30}$alkylcarbonyl,
(e) $C_{2-30}$alkylcarbonyl,
(f) $R^4-O-R^4-$,
(e) substituted $R^4-O-R^4-$ wherein the substituent is phenyl or methoxy,
(f) tetrahydropyran, or
(g) $(R^4)_3$ SiR$^4$, and $R^4$ is independently $C_{1-5}$alkyl at each occurrence.

The claimed invention is also directed to a compound formula (III):

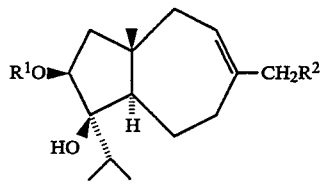

(III)

wherein:

$R^1$ is:
(a) H,
(b) $CH_3$,
(c) $C_{1-30}$alkylcarbonyl,
(d) $C_{2-30}$alkenylcarbonyl,
(e) $CH_3OCH_2$,
(f) $PhCH_2OCH_2$,
(g) $t-BuOCH_2$,
(h) $CH_3OCH_2CH_2OCH_2$, $R^2$ is:
(a) H,
(b) OH,
(c) methoxy,
(d) $C_{1-30}$alkylcarbonyloxy,
(e) $C_{2-30}$alkenylcarbonyloxy, (f) CH₃OCH₂O,
(g) PhCH₂OCH₂O,
(h) t-BuOCH₂O,
(i) CH₃OCH₂CH₂OCH₂O,
provided that when $R^2$ is H, $R^1$ is not H or CH₃CO.

Especially preferred potassium channel agonists are of structural formula (III) wherein:

$R^1$ is:
(a) H,
(b) CH₃,
(c) $C_{1-30}$alkylcarbonyl,
(d) $C_{2-30}$alkenylcarbonyl,
(e) CH₃OCH₂,
(f) PhCH₂OCH₂,
(g) t-BuOCH₂,
(h) CH₃OCH₂CH₂OCH₂, $R^2$ is:
(a) H,
(b) methoxy,
(c) $C_{1-30}$alkylcarbonyloxy,
(d) $C_{2-30}$alkenylcarbonyloxy,
(e) CH₃OCH₂O,
(f) PhCH₂OCH₂O,
(g) t-BuOCH₂O,
(h) CH₃OCH₂CH₂OCH₂O,
provided that when $R^2$ is H, $R^1$ is not H or CH₃CO.

The compounds of the present invention may have asymmetric centers and occur as racemates, racemic mixtures and as individual enantiomers or diastereomers, with all isomeric forms and mixtures thereof being included within the scope of the present invention.

When any variable (e.g., aryl, alkyl, $R^1$, $R^2$, etc.) occurs more than one time in any constituent or in a structural formula, its definition on each occurrence is independent of its definition at every other occurrence. Also, combinations of substituents and/or variables are permissible only if such combinations result in stable compounds.

Also included within the scope of this invention are pharmaceutically acceptable salts or esters, where a basic or acidic group is present in a compound of formula II, such as, for example on the substituted alkyl moiety. When an acidic substituent is present, i.e. —COOH, there can be formed the ammonium, sodium, calcium salt, and the like, for use as the dosage form. Also, in the case of the —COOH group being present, pharmaceutically acceptable esters may be employed, e.g. acetate, maleate, pivaloyloxymethyl, and the like, and those esters known in the art for modifying solubility or hydrolysis characteristics for use as sustained release or prodrug formulations. Where a basic group is present, such as amino, acidic salts such as hydrocholoride, hydrobromide, acetate, pamoate and the like may be used as the dosage form.

As used herein "alkyl" is intended to include both branched- and straight-chain saturated aliphatic hydrocarbon groups having the specified number of carbon atoms and includes methyl (Me), ethyl (Et), propyl (Pr), butyl (Bu), pentyl, hexyl and the like. "Alkoxy" represents an alkyl group of the indicated number of carbon atoms attached through an oxygen bridge. "Cycloalkyl" is intended to include saturated carbon ring groups such as cyclopropyl, cyclobutyl, cyclopentyl, and cyclohexyl (Cyh). "Alkenyl" is intended to include hydrocarbon groups of either a straight or branched configuration with one or more carbon-carbon double bonds which may occur in any stable point along the chain, such as ethenyl, propenyl, butenyl, and the like. "Halo" or "halogen" as used herein means fluoro, chloro, bromo and iodo.

In addition, the invention relates to Compound A:

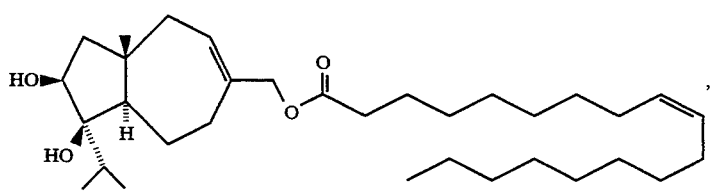

Compound A

The invention is also directed to a compound selected from the group consisting of:

(a)

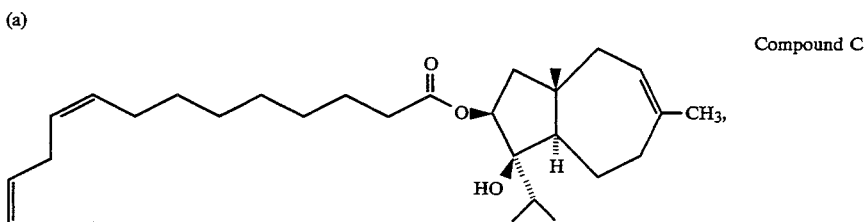

Compound C (b)

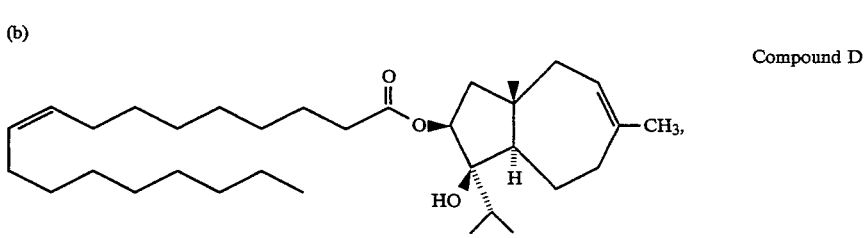

Compound D and (c)

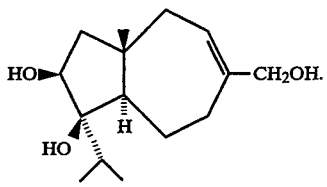

The primary production process used to produce the compounds claimed in the instant invention is through the use of the well known fungal organism *Trichoderma virens* (ATCC 74180). As described in more detail infra, Compound A may be produced in laboratory or large scale quantities utilizing *T. virens* under suitable conditions. This compound may then be purified to a substantially pure form after sufficient and desirable quantities of the potassium channel agonist are produced by *T. virens*. The novel natural product potassium channel agonist isolated from the fungal broth of *T. virens* has the formula:

Compound A

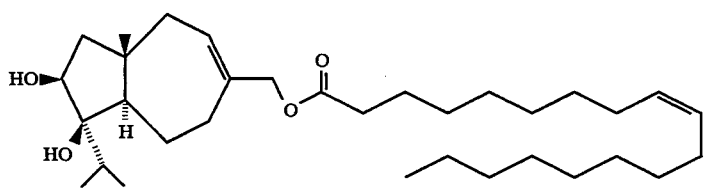

The method of producing the compounds of the present invention comprises:

(a) culturing a fungal organism *Trichoderma virens* (ATCC 74180) so that the fungal organism produces Compound A:

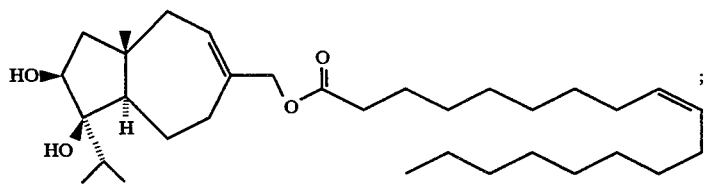

(b) purifying the Compound A; and
(c) optionally reacting the purified product of step (b) with dilute sodium hydroxide to produce a Compound E of the formula:

Compound E

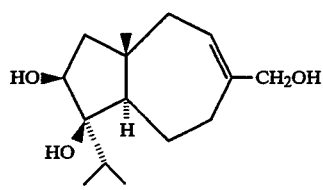

which is further reacted after suitable protection of the vicinal hydroxyl group with a compound selected from a $C_{1-30}$ alkyl or alkenyl anhydride or a $C_{1-30}$ alkyl or alkenyl halide and deprotected to produce a compound with potassium channel agonist activity of the formula:

Compound E (IV)

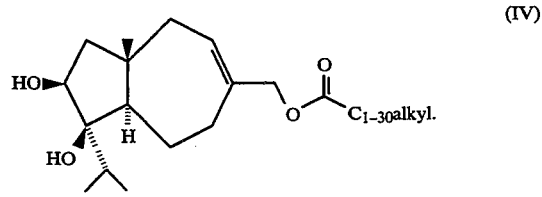

Biological Production of Compound A

The culture Merck Culture Number MF5783 is that of a fungus isolated from sheep dung, near Aborlí, Tarragona, Spain which has been identified as *Trichoderma virens* (Miller, Giddens & Foster) von Arx (Hyphomycetes). This culture exhibits all the essential morphological characteristics of that species (Domsch et al., 1980; Bissett, 1991). In the literature, this fungus is commonly referred to by its synonym *Gliocladium virens* Miller, Giddens & Foster. This culture has been deposited with the American Type Culture Collection at 12301 Parklawn Drive, Rockville, Md. 20852 as ATCC 74180 under conditions of the Budapest Treaty.

The culture MF5783, identified as *Trichoderma virens* exhibits the following morphological features:

Colonies growing rapidly on oatmeal agar (Difco Laboratories), 25° C., 12 hr photoperiod, after 4 days attaining 75–78 mm in diameter, appressed to slightly raised, with downy to radially floccose aerial mycelium, developing scattered, moist conidial pustules in older portions of colonies, dull, with an even, appressed margin, hyaline at margin but soon white, pale yellowish green, Pale Olive Buff, Yellowish Glaucous, to dull green, Corydalis Green, Dark Greenish Glaucous with development of conidial pustules (capitalized color names from Ridgway, 1912). Reverse similar in color. Odors and exudates absent.

Colonies growing moderately fast on Emerson Yp Ss (Difco Laboratories) agar, 25° C., 12 hr photoperiod, after 4 days attaining 40–43 mm diameter, appressed toward margin, slightly raised toward center, obscurely radially striate, also obscurely zonate, with velvety to irregularly floccose aerial mycelium, with margin irregular to minutely fimbriate, appressed, with minute droplets of moist conidia in older regions, mixed with irregular pale greenish gray conidial pustules, hyaline at margin, but soon yellowish green to green, Yellowish Glaucous, Water Green, Deep Lichen Green, Deep Greenish Glaucous, Grape Green, Leaf Green. Reverse similar in color. Odors and exudates absent.

Colonies growing very rapidly on corn meal agar (Difco Laboratories), 25° C., 12 hr photoperiod, after 4 days attaining 80 to >90 mm in diameter, with appressed to radially floccose aerial mycelium, translucent to pale grayish green, with dull green conidial pustules. Reverse translucent. Odors and exudates absent. No growth occurred at 37° C. on on Emerson Yp Ss agar after 7 days.

Conidial pustules forming in irregular, semi-confluent zones, with individual pustules up to 2 mm wide, without sterile appendage protruding from the surface, often with moist conidial droplets on the surface. Conidiophores up to 200 $\mu$m tall, 2–6 $\mu$m wide, indeterminate or determinate, often terminating in a verticillate whorl of conidiogenous cells, unbranched or with 1–4 simple branches, branches dichotomous or verticillate, septate, occasionally with fine incrustations on the walls near the base. Conidiogenous cells, enteroblastic, phialidic, 5–14×3–5 $\mu$m, solitary or in verticils of 2–5, either arising directly from main conidiophore axis, lageniform to ampulliform, symmetrical or eccentric, narrowed at conidiogenous locus, with conidiogenous locus developing a flared collarette in age. Conidia broadly ellipsoid, to obovate or pyriform, sometimes slightly curved, often tapered at proximal end, 5–9×-3–5 $\mu$m, smooth, thin-walled, hyaline to pale green in KOH, adhering together in moist droplets at apex of conidiogenous cells. Chlamydospores abundant on vegetative hyphae after a few days, terminal or intercalary, globose, subglobose to pyriform, 4.5–9 $\mu$m in diameter, smooth, thick-walled, with refractive contents. Hyphae septate, branched, sometime incrusted. References which were helpful in the identification of the above microorganism include Bissett, J. (1991). A revision of the genus Trichoderma. II. Infrageneric classification. Canadian Journal of Botany 69, 2357–2372; Domsch, K. H., W. Gams and T. Anderson. (1980). Compendium of Soil Fungi. Academic Press, London; Hammill, T. M. (1970). *Paecilomyces clavisporis* sp. nov., *Trichoderma saturnisporum* sp. nov., and other noteworthy soil fungi from Georgia. Mycologia 62, 107–122; and Ridgway, R. (1912). *Color Standards and Nomenclature*. Published by the author, Washington, D.C.

The above fungal organism may be used in the production of Compound A which is a potassium channel agonist.

In general the Compounds of structural formulae (I) and (II), particularly Compounds A and B, may be produced by culturing (fermenting) the above described strain, Merck number MF5783 (ATCC 74180), in a solid brown rice-based fermentation medium containing assimilable carbon and nitrogen sources preferably under static aerobic conditions, under constant fluorescent light until a substantial amount of compounds of Compounds A and B is detected in the fermentation extract.

The culture is incubated in a solid brown rice-based medium at a temperature between 20° C. and 37° C., preferably 25° C. for a period of time necessary to complete the formation of Compounds A and B, usually for a period between 3 to 28 days, preferably between 14 to 21 days. In addition, the above described strain can be incubated under submerged aerobic conditions with shaking, preferably on a rotary shaker operating at 220 rpm with a 5 cm throw, with all other incubation parameters remaining the same as for the solid-based medium. The aqueous production medium is maintained at a pH between 5 and 8, preferably about 6.0, at the initiation and termination (harvest) of the fermentation process. The desired pH may be maintained by the use of a buffer such as [2-(N-morpholino) ethanesulfonic acid] monohydrate (MES), 3-(N-morpholino)propane sulfonic acid (MOPS), phosphate buffer and the like, or by choice of nutrient materials which inherently possess buffering properties, such as production media described herein below. The active compound is extracted from the mycelial growth of the culture with an alcoholic or oxygenated solvent, such as an ester or ketone. The preferred solvent for extraction is methyl ethyl ketone (MEK). The solution containing the desired compound is concentrated in vacuo and subjected to chromatographic separation to isolate Compounds A and B from the cultivation medium.

The preferred sources of carbon in the nutrient medium include mannitol, glucose, sucrose, glycerol, xylose, galactose, fructose, lactose, sorbitol, starch, dextrin, other sugars and sugar alcohols, starches and other carbohydrates, or carbohydrates derivatives, and the like. Other sources which may be included are maltose, rhamnose, raffinose, arabinose, mannose, salicin, sodium succinate, acetate, and the like as well as complex nutrients such as brown rice, millet, oat flour, yellow corn meal, rice, cracked corn, and the like. The exact quantity of the carbon source which is utilized in the medium will depend, in part, upon the other ingredients in the medium, but it is usually found that an amount of carbohydrate between 0.5 and 15 percent by weight of the medium is satisfactory. These carbon sources can be used individually or several such carbon sources may be combined in the same medium.

The preferred sources of nitrogen are yeast extract, NZ Amine type E, yellow corn meal, meat extract, peptone, gluten meal, cottonseed meal, soybean meal and other vegetable meals (partially or totally defatted), casein hydrolysates, soybean hydrolysates and yeast hydrolysates, corn steep liquor, dried yeast, wheat germ, feather meal, peanut powder, distiller's solubles, etc., as well as inorganic and organic nitrogen compounds such as ammonium salts (e.g. ammonium nitrate, ammonium sulfate, ammonium phosphate, etc.), urea, amino acids such as serine, alanine, proline, glycine, arginine or threonine, and the like. The various sources of nitrogen can be used alone or in combination in amounts ranging from 0.2 to 10 percent by weight of the medium.

The carbon and nitrogen sources, though advantageously employed in combination, need not be used in their pure form because less pure materials which contain traces of growth factors and considerable quantities of mineral nutrients are also suitable for use. When desired, there may be added to the medium inorganic salts, sodium, potassium, magnesium, calcium, phosphate, sulfate, chloride, carbonate, and like ions which can be incorporated in the culture medium as sodium or calcium carbonate, sodium or potassium phosphate, sodium or potassium chloride, sodium or potassium iodide, magnesium salts, copper salts, cobalt salts, and the like. Also included are trace metals such as cobalt, manganese, iron, molybdenum, zinc, cadmium, copper, and the like. The various sources of inorganic salts can be used alone or in combination in amounts ranging from 0.1 to 1.0, and trace elements ranging from 0.001 to 0.1 percent by weight of the medium.

If necessary, especially when the culture medium foams seriously, a defoaming agent, such as polypropylene glycol 2000 (PPG-2000), liquid paraffin, fatty oil, plant oil, mineral oil or silicone may be added.

Conditions for static solid based fermentation conditions for the production of Compounds A and B are detailed below. In addition, production of these compounds also occurs under submerged aerobic conditions by shaking the culture, preferably at 220 rpm on a rotary shaker with a 5 cm throw. Furthermore, when the growth is carried out in large tanks, it is preferable to use the vegetative form of the organism for inoculation in the production tanks in order to avoid growth lag in the process of production of Compounds A and B. Accordingly, it is desirable first to produce a vegetative inoculum of the organism by inoculating a relatively small quantity of culture medium with spores or mycelia of the organism produced in a "slant" or from previously prepared frozen mycelium and culturing said inoculated medium, also called the "seed medium", and then to transfer the cultured vegetative inoculum aseptically to large tanks. The seed medium, in which the inoculum is produced may be seen in Table 1 and is generally autoclaved to sterilize the medium prior to inoculation. The seed medium is generally adjusted to a pH between 5 and 8, preferably about 6.8, prior to the autoclaving step by suitable addition of an acid or base, preferably as a dilute solution such as hydrochloric acid or sodium hydroxide. Growth of the culture in this seed medium is maintained between 20° C. and 37° C., preferably 25° C. Incubation of culture MF5783 (ATCC 74180) in seed medium (Table 1) is usually conducted for a period of about 2 to 6 days, preferably 3 to 4 days, on a rotary shaker operating at 220 rpm with a 5 cm throw; the length of incubation time may be varied according to fermentation conditions and scales. If appropriate, a second stage seed fermentation may be carded out in the seed medium (Table 1) for greater production of mycelial mass by inoculating fresh seed medium with a portion of the culture growth and then incubating under similar conditions but for a shortened peroid. The resulting growth then may be employed to inoculate the production medium 1, 2 or 3 (Table 2, 3 and 4). The fermentation production medium 1 inoculated with the seed culture growth is incubated for 3 to 28 days usually 14 to 21 days with agitation at 25° C. Agitation and aeration of the culture mixture may be accomplished in a variety of ways. Agitation may be provided by a propeller or similar mechanical agitation equipment, by revolving or shaking the fermentor, by various pumping equipment or by the passage of sterile air through the medium. Aeration may be effected by passing sterile air through the fermentation mixture.

Preferred seed and production media for carrying out the fermentation include the following media as described in Tables 1-4.

TABLE 1
SEED MEDIUM

| | per liter | Trace Element Mix | per liter |
|---|---|---|---|
| Corn Steep Liquor | 5 g | $FeSO_4.H_2O$ | 1 g |
| Tomatoe Paste | 40 g | $MnSO_4.4H_2O$ | 1 g |
| Oat Flour | 10 g | $CuCl_2.2H_2O$ | 25 mg |
| Glucose | 10 g | $CaCl_2$ | 100 mg |
| Trace element mix | 10 mL | $H_3BO_3$ | 56 mg |
| | | $(NH_4)_6Mo_7O_{24}.4H_2O_{19}$ | 19 mg |
| | | $ZnSO_4.7H_2O$ | 200 mg |
| pH = 6.8 | | | |

TABLE 2
Production Medium 1

| Component | Amount (per 250-mL flask) |
|---|---|
| Brown Rice | 10.0 g |
| Yeast Extract | 20.0 mg |
| Sodium Tartrate | 10.0 mg |
| $KH_2PO_4$ | 10.0 mg |
| Distilled Water | 20.0 mL | pH was not adjusted prior to autoclaving for 20 min. Immediately before use, the medium was moistened with 15 mL of water and autoclaved again for 20 min.

TABLE 3
Production Medium 2

| | per liter |
|---|---|
| D-Mannitol | 100 g |
| NZ-Amine (type E) | 33 g |
| FIDCO-Yeast Extract | 10 g |
| Ammonium Sulfate | 5 g |
| Potassium Phosphate (monobasic) | 9 g |
| no pH adjustment | |

TABLE 4
Production Medium 3

| Component | Amount (per 250-ml flask) |
|---|---|
| Millet | 15.0 g |
| Ardamine PH | 0.5 g |
| Sodium Tartrate | 100.0 mg |
| $FeSO_4.7H_2O$ | 10.0 mg |
| Monosodium Glutamate | 100.0 mg |
| Corn Oil | 0.1 mL |
| Distilled Water | 15.0 mL | pH was not adjusted prior to autoclaving for 20 min. Immediately before use, the medium was moistened with 15 ml of water and autoclaved again for 20 min.

Compounds C, D and E are useful as synthetic intermediates in the synthesis of the claimed potassium channel agonists. For example, the vicinal hydroxyl moieties may be protected with a variety of protecting groups including alkyl esters such as those depicted above. The allylic methyl group may then be oxidized to the allylic alcohol which can then be derivatized to form the claimed active esters at $R^2$. The use of the compounds above provides an alterative synthetic route to the compounds of the instant invention.

In addition, Compound A isolated in substantially purified form from the microorganism *Trichoderma virens* (ATCC 74180) can be hydrolyzed to Compound E or derivatives thereof wherein the vicinal hydroxyl moieties are protected with common protecting groups. Compound E and hydroxyl protected derivatives thereof can, in turn, be used in the nonbiological synthetic production of $C_{1-30}$ alkyl esters, or $C_{2-30}$ alkenyl esters which are also useful as potassium channel agonists. Scheme 1 provides a general description of this process. The allylic hydroxyl compound is reacted under suitable basic conditions (to generate an anion) with the activated carbonyl compound of the general formula (XCOC$_{1-30}$alkyl or XCOC$_{2-30}$alkenyl wherein X is a conventional leaving group such as a halogen) to form ester which is deprotected and subsequently used as a potassium channel agonist. The alkyl esters may be selected from, for example, the methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl series of up to thirty carbon atoms and including both saturated and unsaturated systems. The preferred ester is the oleate ester.

SCHEME 1

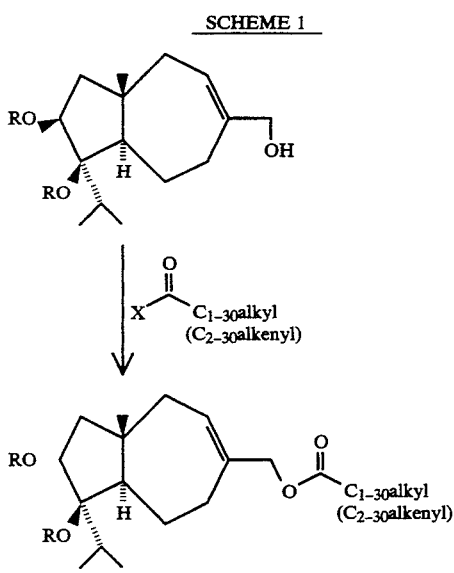

In addition, compounds of formula (II) wherein R$^1$ and R$^3$ together are a substituted or unsubstituted carbon or boron atonm forming a 5-membered ring, wherein the carbon atom may be disubstituted and the boron atom may be monosubstituted may be produced by adding an excess of substituted carboxylic acid or substituted boric acid in ether to an ethereal solution of a compound of structural formula (II) wherein R$^1$ and R$^3$ are both hydroxy. The reaction mixture may be monitored and the product may be recovered by preparatory thin layer chromatography.

The invention is also directed to a method of activating a potassium channel in a mammal, including a human, comprising administering a nontoxic pharmacologically effective amount a potassium channel agonist of the present invention. The potassium channel agonist of the present invention may be administered orally or parenterally in the form of a capsule, a tablet, an injectable preparation or the like. It is usually desirable to use the oral route. Doses may be varied, depending on the age, severity, body weight and other conditions of human patients, but daily dosage for adults is within a range of from about 1 mg to 2000 mg (preferably 5 mg to 200 mg) which may be given in two to four divided doses. Higher doses may be favorably employed as required.

The invention also relates to a method of maintaining or inducing hyperpolarization of a mammalian cell containing a potassium channel comprising the administration to a mammal, including a human, of a nontoxic pharmacologically effective amount of a potassium channel agonist as described in the present invention. The potassium channel agonist of the present invention may be administered orally or parenterally in the form of a capsule, a tablet, an injectable preparation or the like. It is usually desirable to use the oral route. Doses may be varied, depending on the age, severity, body weight and other conditions of human patients, but daily dosage for adults is within a range of from about 1 mg to 2000 mg (preferably 5 mg to 200 mg) which may be given in two to four divided doses. Higher doses may be favorably employed as required.

Furthermore, the invention relates to a method of treating neuronal disorders such as convulsions or ischemia comprising administering to a patient in need of treatment thereof a nontoxic pharmaceutically effective amount of the potassium channel antagonists of the present invention or their pharmaceutically acceptable salts or hydrates. The potassium channel agonist of the present invention may be administered orally or parenterally in the form of a capsule, a tablet, an injectable preparation or the like. It is usually desirable to use the oral route. Doses may be varied, depending on the age, severity, body weight and other conditions of human patients, but daily dosage for adults is within a range of from about 1 mg to 2000 mg (preferably 5 mg to 200 mg) which may be given in two to four divided doses. Higher doses may be favorably employed as required.

The invention further relates to a method of treating smooth muscle disorders such as such as hypertension, asthma, dysmenorrhea, urinary incontinence, and irritable bowel syndrome comprising administering to a patient in need of treatment thereof a nontoxic pharmaceutically effective amount of the potassium channel antagonists of the present invention or their pharmaceutically acceptable salts or hydrates. The potassium channel agonist of the present invention may be administered orally or parenterally in the form of a capsule, a tablet, an injectable preparation or the like. It is usually desirable to use the oral route. Doses may be varied, depending on the age, severity, body weight and other conditions of human patients, but daily dosage for adults is within a range of from about 1 mg to 2000 mg (preferably 5 mg to 200 mg) which may be given in two to four divided doses. Higher doses may be favorably employed as required.

Pharmaceutical compositions comprising a compound of the present invention or a pharmaceutically acceptable salt thereof and a pharmaceutically acceptable carrier may be formed. The pharmaceutically acceptable salts of the compounds of this invention include those formed from cations such as sodium, potassium, aluminum, calcium, lithium, magnesium, zinc and from bases such as ammonia, ethylenediamine, N-methyl-glutamine, lysine, arginine, ornithine, choline, N,N'-dibenzylethelenediamine, chloroprocaine, diethanolamine, procaine, N-benzylphenethylamine, diethylamine, piperazine, tris(hydroxymethyl)aminomethane, and tetramethyl ammonium hydroxide.

EXAMPLE 1

Compounds A and B

Step A: Fermentation of *Trichoderma virens* MF 5783 (ATCC 74180)

Fermentation conditions for the production of Compound A by *Trichoderma virens* MF5783 (ATCC 74180) were as follows. Vegetative mycelia of the culture were prepared by inoculating 54 mL seed medium (Table 1)

in a 250 mL unbaffled Erlenmeyer flask with lyophilized mycelia of MF5783. Seed cultures were incubated for 3 days at 25° C. and 50% relative humidity on a rotary shaker with a 5-cm throw at 220 rpm in a room with constant fluorescent light. Two-mL portions of the 3-day culture were used to inoculate a solid brown rice-based production medium 1 (Table 2) in 250 mL unbaffled Erlenmeyer flasks. The flasks were incubated under static conditions at 25° C. with 50% relative humidity in a room with constant fluorescent light. Maximal production of Compounds A and B on the solid based medium occurs by day 21. At harvest, Compounds A and B were extracted from the cultures with methyl ethyl ketone (70 mL per 250 mL flask and shaken at 220 rpm for 1 hour at 25° C.).

Step B: Isolation of Compound A and Compound B

The solid fermentation broth (2 L WBE) obtained above ($IC_{50}$=10 mL WBE per mL in the $[^{125}I]$ChTX binding assay) was extracted with methyl ethyl ketone. The residue was partitioned between hexane (5.6 g) and methanol (95%, 16.4 g). Successive flash chromatography on $SiO_2$ (methanol-methylene chloride (stepwise elution)) followed by BAKERBOND $C_{18}$ (40 m; methanol-water) yielded two active fractions, corresponding to Compounds A and B. HPLC of the fraction I on Partisil 10 ODS-3 (22×50) using 60% methanol-water (10 ml per min) was carded out to provide Compound B (82 mg; $C_{15}H_{26}O_2$; M.W. 238.1932 (calcd), 238.1965 (found) $IC_{50}$=200 nM); retention time 90 min). Fraction II was also subjected to HPLC on PARTISIL 10 ODS-3 (22×50) using 90% methanol-water to give Compound A (8.5 mg; $C_{33}H_{58}O_4$; M.W. 518.4334 (calcd), 518.4322 (found); $IC_{50}$=360 nM; retention time 258 min). $^1$H NMR ($CD_3OD$, 300 MHz; only prominent peaks indicated) δ 0.88 (d, J=7, 3H), 0.90 (t, 3H), 0.95 (d, J=6.5, 3H), 1.00 (s, 3H), ~1.30 (m), 1.82 (h, J=7, 2H), 2.32 (t, J=7, 2H), 4.02 (dd, J=3, 6.5, 1H), 4.46 (m, 2H), 5.34 (m, 2H), 5.70 (m, 1H). Abbreviations: s=singlet, d=doublet, t=triplet, h=heptet, br=broad, J=$^1$H-$^1$H coupling constant in Hertz (±0.5 Hz). The data were referenced to the solvent peak at δ 3.30 downfield of TMS. $^{13}$C NMR ($CD_3OD$, 100 MHz) 14.5, 17.5, 18.2, 21.3, 22.3, 23.8, 26.2, 28.12, 28.14, 30.2 (2 x), 30.3, 30.4, 30.5, 30.6, 30.8, 30.9, 31.7, 33.1, 35.2, 36.0, 43.2, 43.5, 51.2, 59.6, 71.8, 72.1, 85.1, 129.3, 130.8, 130.9, 139.1, 175.4 ppm. The data were referenced to the solvent peak at 49.0 ppm downfield of TMS. The carbon count of 33 is in agreement with the HR-MS derived molecular formula.

EXAMPLE 2

Preparation of Compounds D and C

To a solution of Compound B (20 mg, $C_{15}H_{26}O_2$, 0.08 mM, produced according to the procedures of Example 1) in triethylamine (0.5 mL), were added 4-dimethylaminopyridine (20 mg, 0.16 mM) and oleic anhydride or linoleic anhydride (175 mg, 0.32 mM). The mixture was purged with $N_2$, sealed, and stirred. The reaction was allowed to proceed at room temperature for 24 h to give Compound D or Compound C, respectively. Ice water (2 mL) was added to the mixture to quench the reaction, and the esters were extracted with ether (2 mL×3). The organic layer was pooled, washed with saturated NaCl (1×2 mL), dried over anhydrous $MgSO_4$, and filtered through a sintered glass. The esters were purified by HPLC on PARTISIL 10 ODS-3 (22×50) using methanol-water (flow rate 10 mL per min; stepwise gradient; 30 min, 80%, 120 min, 90%, and 180 min, 100%). The esters were eluted at 143.6 min (28.0 mg (66.4%)) and 137.5 min (25.9 mg (61.6%)), respectively.

Compound D: $C_{33}H_{58}O_3$, MS (m/z) 502 (M+), 484 (M-18). $^1$H NMR ($CD_2CL_2$, 300 MHz; only prominent peaks indicated) δ 0.84 (d, J=7, 3H), 0.85 (d, J=7, 3H), 0.99 (s, 3H), ~1.26 (m), 1.81 (h, J=7, 1H), 1.96 (dd, J=8.5, 14.5, 1H), 2.29 (t, J=7.5, 2H), 4.99 (dd, J= 2, 8.5, 1H), ~5.32 (m, 2H). Abbreviations: s=singlet, d=doublet, t=triplet, q=quartet, qt=quintet, h=heptet, br=broad, J=$^1$H-$^1$H coupling constant in Hertz (±0.5 Hz). The data were referenced to the solvent peak at δ 5.32 downfield of TMS. $^{13}$C NMR ($CD_2Cl_2$, 100 MHz) 14.3, 17.0, 17.9, 20.9, 21.3, 23.1, 25.4, 27.51 (2 x), 27.55, 29.44, 29.48, 29.52, 29.7 (2 x), 29.9, 30.1, 30.2, 32.3, 34.8, 34.9, 35.5, 42.4, 43.1, 48.0, 58.2, 74.6, 84.6, 122.6, 130.1, 130.3, 139.5, 172.5 ppm. The data were referenced to the solvent peak at 53.8 ppm downfield of TMS. The carbon count of 33 is in agreement with the HR-MS derived molecular formula.

Compound C: $C_{33}H_{56}O_3$, MS (m/z) 500 (M+), 482 (M-18). $^1$H NMR ($CD_2CL_2$, 300 MHz; only prominent peaks indicated) δ 0.85 (d, J=7, 3H), 0.86 (d, J=7, 3H), 0.87 (t, 3H), 1.00 (s, 3H), 1.30 (m), 1.81 (h, J=7, 1H), 1.97 (dd, J=8.5, 14.5, 1H), 2.29 (t, J=7.5, 2H), 2.76 (m, 2H), 5.00 (dd, J=2, 8.5, 1H), ~5.32 (m, 4H). The data were referenced to the solvent peak at δ 5.32 downfield of TMS. $^{13}$C NMR ($CD_2Cl_2$, 100 MHz) 14.2, 17.0, 17.9, 20.9, 21.3, 23.0, 25.4, 26.0, 27.51, 27.54 (2 x), 29.44, 29.49, 29.52, 29.7, 30.0, 31.9, 34.8, 34.9, 35.5, 42.4, 43.1, 48.0, 58.2, 74.6, 84.8, 122.6, 128.2, 128.3, 130.3, 130.5, 139.5, 172.5 ppm. The data were referenced to the solvent peak at 53.8 ppm downfield of TMS. The carbon count of 33 is in agreement with the HR-MS derived molecular formula.

EXAMPLE 3

Preparation of Compound E

Aqueous NaOH (5%, 0.1 mL) was added to an ethanolic solution of Compound A (1.96 mg; 0.0038 mM). The mixture was stirred at room temperature overnight. The solvent was removed, water (1 mL) was added, and the mixture was extracted with $CH_2Cl_2$ (3×1 mL). The pooled solution was washed with saturated NaCl (1×1 mL), dried over anhydrous $MgSO_4$, and the solvent was removed under $N_2$ to give Compound E. It was purified by HPLC on ULTRACARB 5 ODS (30) (4.6×25) using $CH_3CN$-$H_2O$ ($H_2O$, 30 min followed by 40% $CH_3CN$-$H_2O$; flow rate 1 mL/min; retention time 51.5 min).

Compound E: $C_{15}H_{26}O_3$ MS (m/z) 236 (M-$H_2O$, found 236.1777, calculated 236.1776 for $C_{15}H_{24}O_2$) $^1$H NMR ($CD_2Cl_2$, 300 MHz; only prominent peaks indicated) δ 0.87 (d, J=7, 3H), 0.95 (d, J=7, 3H), 1.00 (s, 3H), 1.60 (d, J=4.5, 1H), 1.81 (h, J=7, 1H), 2.11 (dd, J=9, 14.5, 1H),2.24 (m, 1H), 2.38 (d, OH, J=5.5, 1H), 3.96 (d, J=6, 2H), 4.03 (q, J=~5, 1H), 5.61 (m, 1H). The data were referenced to the solvent peak at δ 5.32 downfield of TMS.

EXAMPLE 4

Preparation of

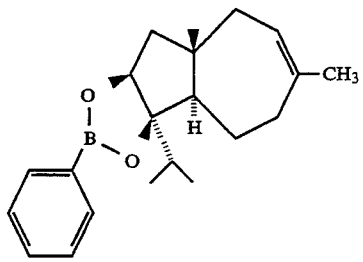

To an ethereal solution of Compound B was added an excess of phenylboric acid (phenylboronic acid) in ether at room temperature. The mixture was stirred for 30 minutes. The reaction was monitored by TLC (SiO$_2$; 5% methanol in methylene chloride; R$_f$: 0.56 for Compound B and 0.88 for the title compound, Compound B phenylborate).

EXAMPLE 5

Potassium Channel Agonist Activity: Electrophysiological Experiments

Patch clamp recordings of currents flowing through large-conductance calcium-activated potassium (maxi-K) channels were made from membrane patches excised from cultured bovine aortic smooth muscle cells using conventional techniques (Hamill et al., 1981, Pflügers Archiv 391, 85–100) at room temperature. Glass capillary tubing (GARNER #7052) was pulled in two stages to yield micropipettes with tip diameters of approximately 1–2 microns. Pipettes were typically filled with solutions containing (mM): 150 KCl, 10 Hepes (4-(2-hydroxyethyl)-1-piperazineethanesulfonic acid), 1 Mg, 0.01 Ca, and adjusted to pH 7.20 with 3.7 mM KOH. After forming a high resistance (>10$^9$ ohms) seal between the sarcolemmal membrane and the pipette, the pipette was withdrawn from the cell forming an excised inside-out membrane patch. The patch was excised into a bath solution containing (mM): 150 KCl, 10 Hepes, 5 EGTA (ethylene glycol bis($\beta$-aminoethyl ether)-N,N,N',N'-tetraacetic acid), sufficient Ca to yield a free Ca concentration of 1–5 $\mu$M, and the pH was adjusted to 7.2 with 10.5 KOH. For example, 4.568 mM Ca was added to give a free concentration of 2 $\mu$M at 22° C. An Axopatch 1C amplifier (Axon Instruments, Foster City, Calif.) with a CV-4 headstage was used to control the voltage and to measure the currents flowing across the membrane patch. The input to the headstage was connected to the pipette solution with a Ag/AgCl wire, and the amplifier ground was connected to the bath solution with a Ag/AgCl wire covered with a robe filled with agar dissolved in 0.2M KCl. Maxi-K channels were identified by their large single channel conductance (~250 pS) and sensitivity of channel open probability to membrane potential and intracellular calcium concentration.

Planar lipid bilayers were formed from a solution of 1-palmitoyl-2-oleoylphosphatidylethanolamine (POPE) and 1-palmitoyloleoylphosphatidylcholine (POPC) in a 7/3 molar ratio dissolved in decane (50 mg/mL). This lipid solution was painted across a small hole (250 micron) separating two aqueous compartments and readily formed bilayers with capacitances of 200–250 pF. The solution on the side that the membranes were added (cis) contained (mM): 150 KCl, 10 Hepes, 0.01 Ca, 3.7 KOH, pH 7.20. The solution on the other side (trans) contained (mM): 25 KCl, 10 HEPES, 0.01 Ca, 3.7 KOH, pH 7.20. Plasma membrane vesicles purified from bovine aortic smooth muscle (Slaughter et al. 1989, Biochemistry 28, 3995–4002) were added to the cis side until channel incorporation occurred. After channel incorporation, the concentration of KCl on the trans side was increased to 150 mM to prevent further channel incorporation. The orientation of maxi-K channels after insertion into the bilayer was determined from the calcium and voltage sensitivity of the channel. Increases in calcium or voltage on the intracellular side lead to increases in channel open probability. An Axopatch 1C with a CV-4B headstage was used to control the membrane potential and record currents flowing across the bilayer. The inputs to the amplifier were connected to Ag/AgCl wires which connected to the two sides of the bilayer chamber through small tubes filled with agar dissolved in 0.2M KCl. Experiments were done at room temperature.

Data was stored on a RACAL STORE 4DS FM tape recorder (Racal Recorders, Vienna, Va.) or on digital video tape using a video casette recorder after digitizing the signal with VR-10 (Instrutech Corp., Belmont N.Y.) PCM video encoder. The signal was also recorded on chart paper with a GOULD 2400S chart recorder (Gould Inc., Cleveland Ohio). For quantitative analysis, the data was played into a DEC 11-73 (Digital Equipment Corp., Maynard, Mass.) after digitization with a DT2782-8D1A analogue to digital converter (Data Translation Inc., Marlboro, Mass.), or played into a MAC IIx or QUADRA 700 computer (Apple Computers) after digitization with an ITC-16 interface (Instrutech Corp., Belmont, N.Y.).

The effects of Compound A on maxi-K channels were examined in excised inside-out membrane patches and in lipid bilayers. In patch clamp experiments, 10 $\mu$M Compound A caused clear increases in channel open probability that developed slowly over 5–10 minutes. Specifically, 10 $\mu$M Compound A caused a 2.1 fold increase in channel open probability. These increases in channel open probability were slowly reversed after long (20–60 minutes) washout. In lipid bilayer experiments, addition of 10 $\mu$M Compound A to the outside face of the channel did not increase channel open probability. In contrast, 10 $\mu$M Compound A to the inside face of the channel caused a 1.4 fold increase in channel open probability, suggesting that this compound is more effective when added to the inside than the outside.

The effects of four related compounds, Compound D, Compound C, Compound E and Compound B on Maxi-K channels were investigated in excised, inside-out patch clamp recordings. Application of 10 $\mu$M Compound C or Compound D to the intracellular side of the channel caused small decreases in channel open probability. Application of 10 $\mu$M Compound E to the intracellular side had no observable effect on channel open probability. Compound B had no clear effect on channel open probability at 10 $\mu$M.

EXAMPLE 6

Biochemical Experiments

The interaction of [$^{125}$I]ChTX (Charybdotoxin) with bovine aortic sarcolemma membrane vesicles was determined under conditions as described in Vazquez et al., 1989, J. Biol. Chem. 264, 20902–20909. Briefly, sarcolemma membrane vesicles were incubated in 12×75 polystyrene robes with ca. 25 pM [$^{125}$I]ChTX (2200 Ci/mmol), in the absence or presence of test compound, in a media consisting of 20 mM NaCl, 20 mM Tris-HCl pH 7.4, 0.1% bovine serum albumin, 0.1% digitonin. Nonspecific binding was determined in the presence of 10 nM ChTX. Incubations were carried out at room temperature until ligand binding equilibrium is achieved at ca. 90 min. At the end of the incubation period, samples were diluted with 4 mL ice-cold 100 mM NaCl, 20 mM Hepes-Tris pH 7.4 and filtered through GF/C glass fiber filters that have been presoaked in 0.5% polyethylenimine. Filters were rinsed twice with 4 mL ice-cold quench solution. Radioactivity associated with filters was determined in a gamma counter. Specific binding data in the presence of each compound (difference between total binding and nonspecific binding) was assessed relative to an untreated control.

Compound A caused a concentration-dependent inhibition of [$^{125}$I]ChTX binding. The concentration of compound needed to cause 50% inhibition of binding is ca. 360 nM. Compound D and Compound C were tested at three different concentrations: 1, 10 and 100 μM. Compound D caused a significant inhibition of binding when tested at 100 μM. At this concentration, binding was 37% of that under control conditions. Compound C had no effect on binding at concentrations up to 100 μM. Compound E did not produce any significant effect on toxin binding in the range of concentrations from 1 nM to 100 μM. Compound B caused a concentration-dependent inhibition of [$^{125}$I]ChTX binding with half-maximal inhibition taking place at a concentration of 200 nM.

EXAMPLE 7

Oral Formulation

As a specific embodiment of an oral composition of a potassium channel agonist of the present invention, 100 mg of Compound A is formulated with a sufficient amount of finely divided lactose to provide a total amount of 580 to 590 mg to fill a size 0 hard gelatin capsule.

The previous examples are non-limiting and clearly demonstrate that the compounds as claimed in the present application are useful as either Maxi-K potassium channel agonists or as synthetic intermediates in the production of said agonists. In addition, the claimed invention relates to novel microbiological processes for producing the claimed compounds.

What is claimed is:

1. A compound of the formula:

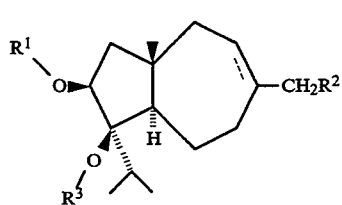

(II)

and its pharmaceutically acceptable salts, wherein:
$R^1$ is:
(a) H,
(b) $C_{1-5}$alkyl,
(c) $C_{2-5}$ alkenyl (d) $C_{1-30}$alkylcarbonyl,
(e) $C_{2-30}$ alkenylcarbonyl,
(f) $R^4$—O—$R^4$—,
(e) substituted $R^4$—O—$R^4$— wherein the substituent is phenyl or methoxy,
(f) tetrahydropyran, or
(g) $(R^4)_3$ Si—$R^4$— wherein $R^4$ is independently $C_{1-5}$alkyl or $C_{2-5}$ alkenyl at each occurrence, $R^3$ is:
(a) H,
(b) $C_{1-5}$alkyl,
(c) $C_{2-5}$ alkenyl
(d) $C_{1-30}$alkylcarbonyl,
(e) $C_{2-30}$alkenylcarbonyl,
(e) $R^4$—O—$R^4$—,
(f) substituted $R^4$—O—$R^4$— wherein the substituent is phenyl or methoxy,
(g) tetrahydropyran, or
(h) $(R^4)_3$ SiR$^4$, or $R^1$ and $R^3$ together with the adjacent oxygen and ring carbon atoms, form a five-membered ting wherein $R^1$ and $R^3$ together are a single substituted or unsubstituted carbon or boron atom, wherein the carbon atom is substituted with two substituents independently selected from:
(a) H,
(b) $C_{1-4}$ alkyl,
(c) $C_{2-5}$ alkenyl,
(d) $C_{1-6}$ alkoxy,
(e) $C_{2-6}$ alkenyloxy, and
(f) phenyl, and wherein the boron atom is substituted with one substituent selected from:
(a) H,
(b) $C_{1-4}$ alkyl,
(c) $C_{2-5}$ alkenyl,
(d) $C_{1-6}$ alkoxy,
(e) $C_{2-6}$ alkenyloxy, and
(f) phenyl;

$R^2$ is:
(a) H,
(b) OH,
(c) $C_{1-5}$alkyloxy,
(d) $C_{2-5}$ alkenyloxy,
(e) $C_{1-30}$alkylcarbonyloxy,
(f) $C_{2-30}$alkenylcarbonyloxy,
(g) $R^4$—O—$R^4$—O—,
(h) substituted $R^4$—O—$R^4$—O— wherein the substituent is phenyl or methoxy,
(i) tetrahydropyran-oxy, or
(j) $(R^4)_3$ Si—$R^4$—, provided that when $R^2$ is H and $R^3$ is H, $R^1$ is not H or $CH_3CO$; $R^4$ is independently $C_{1-5}$alkyl or $C_{2-5}$ alkenyl at each occurrence, and the dashed line indicates the optional presence of a double bond.

2. The compound according to claim 1 of the formula:

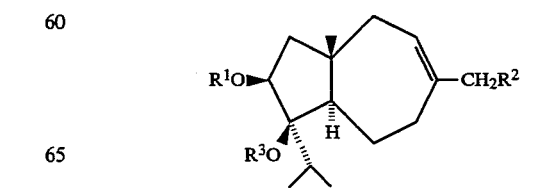

wherein:

$R^1$ is:
(a) H,
(b) $CH_3$,
(c) $C_{1-30}$alkylcarbonyl,
(d) $C_{2-30}$alkenylcarbonyl
(e) $CH_3OCH_2$,
(f) $PhCH_2OCH_2$,
(g) $t\text{-}BuOCH_2$,
(h) $CH_3OCH_2CH_2OCH_2$,
(i) tetrahydropyran, or
(j) $Me_3SiCH_2CH_2$;

$R^2$ is:
(a) H,
(b) OH,
(c) methoxy,
(d) $C_{1-30}$alkylcarbonyloxy,
(e) $C_{2-30}$alkenylcarbonyloxy,
(f) $CH_3OCH_2O$,
(g) $PhCH_2OCH_2O$,
(h) $t\text{-}BuOCH_2O$,
(i) $CH_3OCH_2CH_2OCH_2O$,
(j) tetrahydropyranoxy, or
(k) $Me_3SiCH_2CH_2O$, provided that when $R^2$ is H and $R^3$ is H, $R^1$ is not H or $CH_3CO$; and $R^3$ is:
(a) H,
(b) $C_{1-5}$alkyl,
(c) $C_{2-5}$ alkenyl
(d) $C_{1-30}$alkylcarbonyl,
(e) $C_{2-30}$alkylcarbonyl,
(f) $R^4$—O—$R^4$—,
(e) substituted $R^4$—O—$R^4$— wherein the substituent is phenyl or methoxy,
(f) tetrahydropyran, or
(g) $(R^4)_3 SiR^4$, and
$R^4$ is independently $C_{1-5}$alkyl at each occurrence.

3. The compound according to claim 1 of the formula:

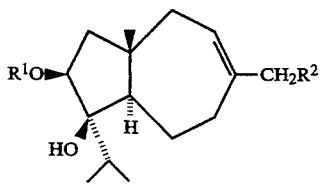

wherein:
$R^1$ is:
(a) H,
(b) $CH_3$,
(c) $C_{1-30}$alkylcarbonyl,
(d) $C_{2-30}$alkenylcarbonyl,
(e) $CH_3OCH_2$,
(f) $PhCH_2OCH_2$,
(g) $t\text{-}BuOCH_2$,
(h) $CH_3OCH_2CH_2OCH_2$, $R^2$ is:
(a) H,
(b) OH,
(c) methoxy,
(d) $C_{1-30}$alkylcarbonyloxy,
(e) $C_{2-30}$alkenylcarbonyloxy,
(f) $CH_3OCH_2O$,
(g) $PhCH_2OCH_2O$,
(h) $t\text{-}BuOCH_2O$,
(i) $CH_3OCH_2CH_2OCH_2O$, provided that when $R^2$ is H, $R^1$ is not H or $CH_3CO$.

4. The compound according to claim 1 of the formula:

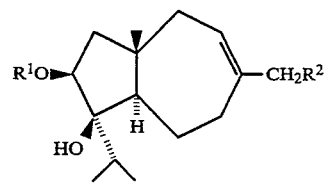

wherein:
$R^1$ is:
(a) H,
(b) $CH_3$,
(c) $C_{1-30}$alkylcarbonyl,
(d) $C_{2-30}$alkenylcarbonyl,
(e) $CH_3OCH_2$,
(f) $PhCH_2OCH_2$,
(g) $t\text{-}BuOCH_2$,
(h) $CH_3OCH_2CH_2OCH_2$, $R^2$ is:
(a) H,
(b) methoxy,
(c) $C_{1-30}$alkylcarbonyloxy,
(d) $C_{2-30}$alkenylcarbonyloxy,
(e) $CH_3OCH_2O$,
(f) $PhCH_2OCH_2O$,
(g) $t\text{-}BuOCH_2O$,
(h) $CH_3OCH_2CH_2OCH_2O$, provided that when $R^2$ is H, $R^1$ is not H or $CH_3CO$.

5. The compound according to claim 3 of the formula:

(a)

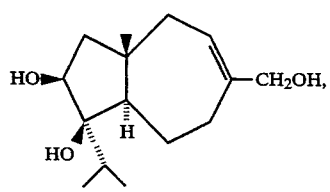

(b)

-continued

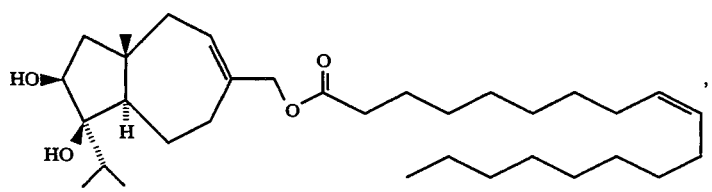

(c)

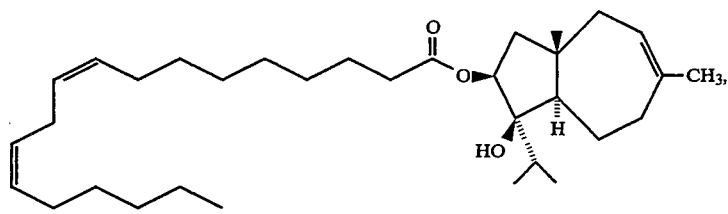

or (d)

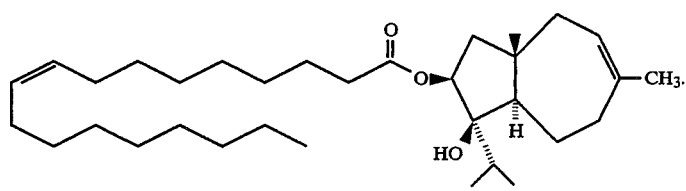

6. The compound according to claim 3 of the formula:

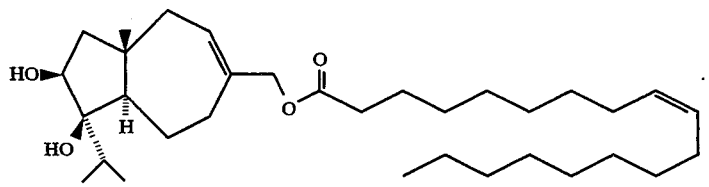

7. A pharmaceutical composition comprising a compound according to claim 4 and a pharmaceutically acceptable carrier.

8. A pharmaceutical composition for activating a calcium-activated potassium channel in a mammal, including a human, comprising a compound as claimed in claim 4 and a pharmaceutically acceptable carrier.

* * * * *